United States Patent [19]

Black et al.

[11] 4,320,142
[45] Mar. 16, 1982

[54] N-[(PHENYL(OXY OR AMINO))THIOACETYL]-1,2-DIAMINE ANTHROPODICIDES

[76] Inventors: Malcolm H. Black, 9 Longfield Gardens, Tring, Herts.; Alexander D. Frenkel, 13 New Rd., Aston Clinton, Bucks.; Peter T. Roberts, 66 Bridgewater Rd., Berkhamsted, Herts, all of England

[21] Appl. No.: 150,065

[22] Filed: May 15, 1980

[30] Foreign Application Priority Data

May 17, 1979 [GB] United Kingdom ............... 17156/79
Feb. 28, 1980 [GB] United Kingdom ............... 05886/80

[51] Int. Cl.³ ................. C07C 157/09; C07C 155/02; C07C 153/063; A01N 47/30; A01N 47/28; A01N 47/10; A01N 47/22; A01N 47/40
[52] U.S. Cl. .................................... 424/300; 560/10; 560/16; 564/27; 564/47; 564/48; 564/52; 564/53; 564/54; 564/55; 564/56; 564/74; 260/453.3; 260/453.4; 260/453.5; 260/453.6; 260/453.8; 260/453.9; 260/453.99; 260/455 A; 260/465 D; 260/465 E; 424/298; 424/304; 424/322; 424/324
[58] Field of Search ............... 560/10, 16; 260/465 D, 260/465 E, 453 A, 453 RW, 455 A, 453.3, 453.4, 453.5, 453.6, 453.8, 453.9, 453.99, 1; 424/300, 298, 304, 309, 322, 324; 564/74, 52, 53, 54, 55, 56, 47, 48, 27

[56] References Cited

U.S. PATENT DOCUMENTS 2,579,478 12/1951 Djeraassi ............................... 564/74
3,647,413 3/1972 Rumanowski ........................ 564/74
3,725,452 4/1973 Rumanowski ........................ 564/74
4,131,449 12/1978 Entwistle ............................... 564/74
4,226,876 10/1980 Copp ..................................... 564/74

FOREIGN PATENT DOCUMENTS 862022 6/1978 Belgium .
1647 5/1979 European Pat. Off. .
2756638 6/1978 Fed. Rep. of Germany .
1374682 4/1964 France .
2023603 1/1980 United Kingdom .

Primary Examiner—Natalie Trousof
Assistant Examiner—Michael Shippen
Attorney, Agent, or Firm—Donald Brown

[57] ABSTRACT

Compounds of formula (I) are pesticides active against arthropods.

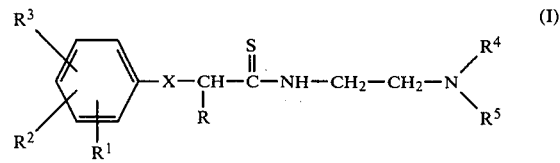

wherein
$R^1$, $R^2$, and $R^3$ are H, alkyl, alkoxy, halo, CN or $CF_3$ or two are linked to form a 3 or 4 carbon atom group;
X is O or NA where A is H or alkyl;
R is H or alkyl;
$R^4$ is H or optionally substituted alkyl, aryl, aralkyl, alkenyl or alkynyl; and
$R^5$ is —CB. $R^6$ where B is O, S or $NR^7$ where $R^7$ is H, alkyl, alkoxy, or optionally substituted aryl or aralkyl;
$R^6$ is H, $R^8$, $OR^8$, $SR^8$ or $NR^9R^{10}$ where $R^8$ is alkyl, alkenyl or optionally substituted aryl, aralkyl or aryloxyalkyl; and $R^9$ and $R^{10}$ are H, alkyl or optionally substituted aryl or aralkyl;

The invention also comprises processes for the preparation of compounds (I), formulations containing them, and their use as pesticides.

40 Claims, No Drawings

N-[(PHENYL(OXY OR AMINO))THIOACETYL]-1,2-DIAMINE ANTHROPODICIDES

This invention relates to novel amides, processes for their preparation, intermediates useful in those processes, pesticidal formulations containing the amides, and their use as pesticides.

Compounds of formula (I) below have activity against Arthropods, in particular against members of the Order Acarina.

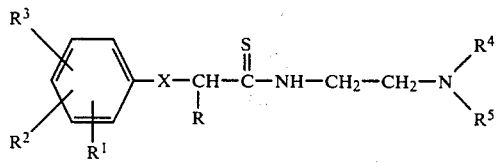

In formula (I), $R^1$, $R^2$ and $R^3$ are the same or different and are selected from hydrogen, alkyl, alkoxy, halo, cyano and trifluoromethyl or two of $R^1$, $R^2$ and $R^3$ are linked to form a 3 or 4 carbon atom group;

X is O or NA where A is hydrogen or alkyl;

R is hydrogen or alkyl;

$R^4$ is hydrogen; alkyl; substituted alkyl wherein the substituent(s) are selected from halo, hydroxy, cyano, alkoxy, aryloxy, alkylthio, arylthio and substituted amino; alkynyl; alkenyl; haloalkenyl; aralkyl; aryl; or a substituted aryl or aralkyl group where the substituents are selected from alkyl, alkoxy, halo, cyano and trifluoromethyl; and $R^5$ is a group

where B is O, S or $NR^7$ where $R^7$ is hydrogen, CN, alkoxy, alkyl, aralkyl, aryl or a substituted aryl or aralkyl group where the substituents are selected from alkyl, alkoxy, halo, cyano and trifluoromethyl; and $R^6$ is hydrogen or a group $R^8$, $OR^8$, $SR^8$ or $NR^9R^{10}$ where $R^8$ is alkyl, aryloxyalkyl, alkenyl, aralkyl, aryl or a substituted aryl, aralkyl or aryloxyalkyl group where the substituents are selected from alkyl, alkoxy, halo, cyano and trifluoromethyl, and $R^9$ and $R^{10}$ are the same or different and are selected from hydrogen, alkyl, aralkyl, aryl or substituted aryl or aralkyl where the substituents are selected from alkyl, alkoxy, halo, cyano and trifluoromethyl.

Certain compounds of formula (I) where X is NA or B is $NR^7$ and intermediates as hereinafter defined are able to form acid addition salts, and references to such compounds include references to acid addition salts unless the conext clearly indicates otherwise.

When used herein, 'alkyl' and 'alkoxy' mean a straight or branched alkyl or alkoxy group, respectively, having from 1 to 20 such as 1 to 5 carbon atoms, such as methyl and methoxy; 'halo' means fluoro, chloro, bromo or iodo; 'alkenyl' means an alkenyl group having from 2 to 20 carbon atoms, and having one or more double bonds, such as prop-2-enyl; 'aryl' means phenyl or naphthyl; and 'aralkyl' means alkyl substituted by an aryl group, such as benzyl. When $R^4$ is alkenyl, it is an alkenyl group which is saturated in the 1-position.

One preferred sub-group or compounds of formula (I) are those of formula (II):

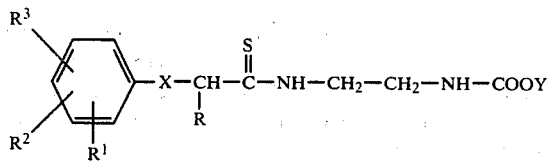

wherein $R^1$, $R^2$, $R^3$, R and X are as defined above and Y is alkyl, alkenyl aryl or aralkyl.

Preferred compounds of formulae (I) and (II) are those having one or more of the following features:

X is O or NH;

R is hydrogen or methyl;

$R^1$ is in the 2-position and $R^2$ is in the 3-position, particularly those where $R^3$ is hydrogen and at least one of $R^1$ and $R^2$ is halo or alkyl;

$R^4$ is hydrogen;

Y is alkyl aryl or aralkyl, such as ethyl; phenyl or benzyl

B is S; and $R^6$ is optionally substituted phenylamino.

The compound of formula (I) may be made by any method known for making compounds having analogous functional groups. These methods include:

(a) the reaction of a compound of formula (III):

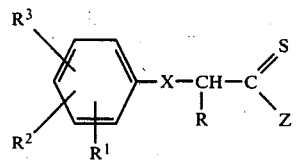

wherein $R^1$, $R^2$, $R^3$, X and R are as defined in formula (I) and Z is a leaving group such as alkoxy, alkylthio, aralkoxy, aralkylthio or mercapto with a compound of formula (IV):

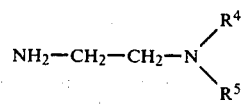

or a salt thereof wherein $R^4$ and $R^5$ are as defined in formula (I):

(b) the reaction of a phenol or aniline of formula (V):

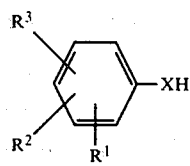

or an O- or N- metal derivative thereof (such as an alkali metal derivative) wherein X, $R^1$, $R^2$ and $R^3$ are as defined in formula (I) with a compound of formula (VI):

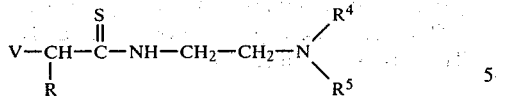

wherein R, R⁴ and R⁵ are as defined in formula (I) and V is a leaving group derived from a suitable organic or inorganic acid, such as halo (e.g. chloro, bromo or iodo), alkylsulphonyloxy or arylsulphonyloxy (e.g. p-toluenesulphonyloxy);

(c) the reaction of a compound of formula (VII):

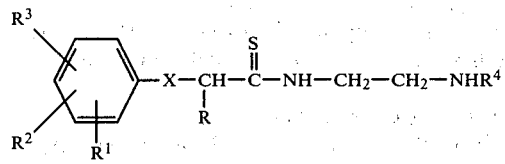

wherein R¹, R², R³, X, R and R⁴ are as defined in formula (I) with a compound of formula (VIII):

W-R⁵ wherein R⁵ is as defined in formula (I) and W is a leaving group such as halo;

(d) the reaction of a compound of formula (IX):

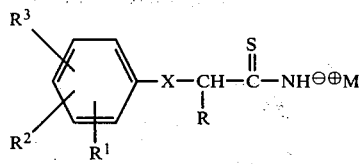

wherein R¹, R², R³, X and R are defined in formula (I) and M⊕ is one equivalent of a metal ion, such as K⁺ or Na⁺ with a compound of formula (X):

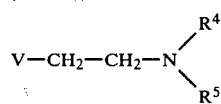

wherein R⁴ and R⁵ are as defined in formula (I) and V is as defined in relation to formula (VI);

(e) for those compounds where B is S, the reaction of a compound of formula (XI):

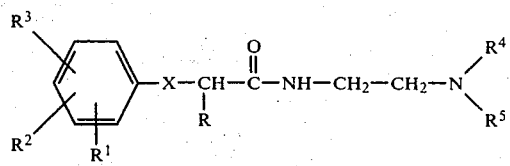

wherein R¹, R², R³, X, R, R⁴ and R⁵ are as defined in formula (I) with P₂S₅ or other suitable inorganic sulphides;

(f) for those compounds where R⁴ is hydrogen, the reaction of a compound of formula (XII):

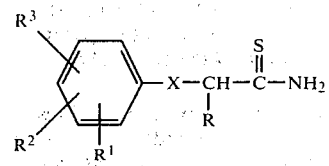

wherein R¹, R², R³, X and R are as defined in formula (I) or a compound of formula IX as hereinbefore defined with a compound of formula (XIII):

wherein
R⁵ is as defined in formula (I); and
(g) for those compounds where B is O or S and R⁶ is NR⁹R¹⁰ where R⁹ is hydrogen, the reaction of a compound of formula (XIV):

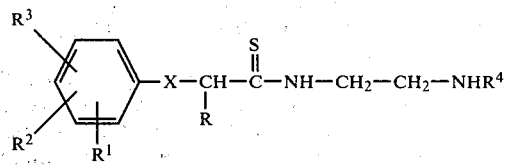

wherein R¹, R², R³, X, R and R⁴ are as defined in formula (I) with a compound of formula (XV):

R¹⁰—N=C=B wherein R¹⁰ is as defined in formula (I) and B is O or S.

Process (a) will normally be effected in a dry aprotic solvent, such as ether, chloroform or dichloromethane, at a moderate temperature, such as −30° to 50° C., e.g. at ambient temperature.

Processes (b) and (d) will normally be effected in a dry polar solvent, such as a ketone, e.g. butanone, preferably at an elevated temperature, e.g. at reflux.

Process (c) will normally be effected in a dry polar solvent, such as ether or dichloromethane, at ambient or depressed temperature, e.g. −20° C. to room temperature.

Process (e) will normally be effected in a dry aprotic solvent, such as benzene or pyridine, at ambient or elevated temperature, e.g. at reflux.

Process (f) will normally be effected in an anhydrous solvent at an elevated temperature, such as refluxing tetralin or diphenyl, in the presence of aluminium trichloride.

Process (g) will normally be effected in a dry aprotic solvent, such as ether, at ambient or depressed temperature, such as −20° C. to room temperature, e.g. about 0° C.

The anilino compounds of formula (I) may be isolated from the reaction mixture as the free base or in the form of an acid addition salt. The bases may be converted into acid addition salts thereof by known techniques with the aid of the appropriate acid, and salts of the compounds may also be converted into the free bases or into other acid addition salts.

For use as a pesticide, the anilino compounds of formula (I) may be presented in the form of their free bases, or as acid addition salts thereof. Suitable salts of formula (I) include hyrohalide, sulphate, nitrate, phosphate, thiocyanate, acetate, propionate, stearate, naphthenate, perchlorate, benzoate, methanesulphonate, ethanesulphonate, tosylate and benzenesulphonate acid addition salts thereof.

The compounds of formula (I) may be used to combat insects, ticks, mites, and other arthropods including free living arthropods and those which are ectoparasites of plants, mammals and birds. They are especially useful for the control of acarine ectoparasites of animals, particularly those ticks of the genera Boophilus, Rhipicephalus, Amblyomma, Hyalomma, Ixodes, Haemaphysalis, Dermacentor, and Anocentor; mites of veterinary importance, such as Psoroptes spp., Psorergates, spp., Sarcoptes spp., Chorioptes spp. and Demodex spp., e.g. the sheep scab mite *Psoroptes ovis;* and other ectoparasites of the sub-Orders Ixodoidea and Sarcoptiformes; and Tetranychus species on plants. Such ectoparasites infest stock and domestic animals and fowls, depending upon the location of the host and the particular ectoparasites. Common hosts are cattle, pigs, sheep, goats, horses, camels, chickens, dogs and cats.

The compounds of formula (I) may be used alone or in combination with an additive which may take the form of one or more of the carriers used in the formulation art, such as; wetting, diluting, stabilising, thickening, emulsifying, dispersing or surface active agents or other standard carrier ingredients.

A formulation may be an aqueous solution of an acid addition salt of a compound of formula (I), or a suspension of a compound of formula (I) in water, and may be used alone or in combination with suitable surface active agents. The formulation per se may be used alone or diluted in water for application to the pests or their immediate environment by way of spraying, dipping, or other known means of application.

A formulation may be in the form of a water-miscible oil comprising a compound of formula (I) per se or, when X is NA, or B is $NR^7$, with an equimolar quantity of a suitable organic acid, such as oleic acid or naphthenic acid, to provide a salt soluble in organic solvents and emulsifiers, and is applied as an emulsion by way of spraying or dipping.

A formulation may be a non-aqueous solution or suspension of compound (I) in a suitable organic solvent for the direct application by the 'pour-on' method. A formulation may also take the form of a wettable powder for dilution with water and application by dipping or spraying. Other solid formulations may also be used for direct application without dilution such as dusts, powders and granules.

Formulations may also be in the form of an aerosol, a foam or an impregnated article, such as a tag or collar. These may be prepared using conventional techniques.

A further formulation may be a paste, grease or gel containing a compound of formula (I) and a suitable carrier, and may be applied by spreading the formulation over the infested area.

A compound of formula (I) is preferably present in a pesticidal formulation in an amount between 1 and 80%, particularly preferred formulations containing about 20%, calculated by weight of the compound (I) per se. The concentration of a compound of formula (I) applied to the pests or their immediate invironment may be in the range of 0.001%–20%, calculated by weight of the compound (I) per se.

It will be appreciated from the foregoing that what we will claim may comprise any novel feature described herein, principally and not exclusively, for example:

(a) A compound of formula (I);

(b) A method of preparation of a compound of formula (I)

(c) A method of controlling arthropod pests, particularly members of the Order Acarina, by applying to the pest or the pest's environment a compound of formula (I):

(d) A pesticidal formulation comprising a compound of formula (I) and a carrier therefor.

(e) A method of making a formulation comprising admixture of a carrier and a compound of formula (I).

(f) A compound of formula (I) for use as a pesticide.

(g) Novel intermediates used in processes (a)-(g).

EXAMPLE 1

N-[(2,3-Dimethylphenoxy)thioacetyl]-N'-ethoxycarbonylethane-1,2-diamine (i) A stirred suspension of ethyl (2,3-dimethylphenoxy)acetimidate hydrochloride (13 g) in dry ether (100 ml) was treated with dry triethylamine (5.39 g). The resultant mixture was treated with dry gaseous hydrogen sulphide for 2 hours at 0° and set aside at 0°–5° overnight. The resulting solids were removed by filtration and the filtrate evaporated to dryness to yield ethyl thiono (2,3-dimethylphenoxy)acetate as a colourless solid, m.p. 39°–40°.

(ii) A solution of N-ethoxycarbonylethane-1,2-diamine (2 g) in dry chloroform (10 ml) was added dropwise to a stirred solution of ethyl thiono (2,3-dimethylphenoxy) acetate (3.4 g) in dry chloroform (30 ml) at ambient temperature. After stirring overnight the solvent was removed under reduced pressure and the resulting solid recrystallised from isopropanol to yield the title product, 104°–105° C.

EXAMPLE 2

N-[(2,3-dimethylphenoxy)thioacetyl]-N'-phenylthiocarbamoyl-1,2-diaminoethane.

(i) A solution of ethyl thiono-(2,3-dimethylphenoxy)-acetate (2.85 g, 5% molar excess) in dry ether (10 ml) was added dropwise to a stirred ethereal solution (30 ml) of dry 1,2-diaminoethane (0.69 g) at 0° C. After 1–2 hours tlc analysis indicated completion of reaction.

(ii) The ethereal solution resulting from the previous reaction was treated with an equimolar solution of phenyl isothiocyanate (1.55 g) in dry ether (10 ml) at 0° C. and the stirred reaction mixture allowed to rise to ambient temperature overnight. The title compound was recovered by filtration and subsequent vacuum desiccation; mp 112°–113° C.

EXAMPLES 3 TO 10

By methods analogous to those described in Examples 1 and 2 above, the compounds of examples 3 to 10 below were prepared.

EXAMPLE 3

N-[(2,3-dimethylphenoxy)-thioacetyl]-N'-(benzyloxycarbonyl)-ethane-1,2-diamine; mp 91°–92° C.

EXAMPLE 4

N-[(2,3-dimethylphenoxy)-thioacetyl]-N'-(4-chlorophenyl carbamoyl)ethane-1,2-diamine; mp 110° C.

EXAMPLE 5

N-[(2,3-dimethylphenoxy)-thioacetyl]-N'-(methylthiocarbamoyl)ethane-1,2-diamine; mp 120° C.

EXAMPLE 6

N,N'-Bis[(2,3-dimethylphenoxy)-thioacetyl]-ethane-1,2-diamine; mp 168° C.

EXAMPLE 7

N-[(2,3-dimethylphenoxy)thioacetyl]-N'-acetyl-ethane-1,2-diamine; mp 119°–121° C.

EXAMPLE 8

N-[(2,3-dimethylphenoxy)-thioacetyl]-N'-[3-phenoxybenzyloxycarbonyl]-ethane-1,2-diamine; mp 76° C.

EXAMPLE 9

N-[(2,3-dimethylphenoxy)-thioacetyl]-N'-(4-methoxybenzoyl)-ethane-1,2-diamine; mp 148°–149° C.

EXAMPLE 10

N-[(2,3-dimethylphenoxy)-thioacetyl]-N'-(N''-methyl-N''-phenylcarbamoyl) ethane-1,2-diamine; mp 111°–113° C.

EXAMPLE 11

Engorged female ticks of the Biarra Strain of *Boophilus microplus* are immersed in groups of 20 ticks per concentration in a range of dilutions of the compound under test. The wash is prepared immediately prior to the test by dilution (with water) of the compound under test. The constituents may be in the form of miscible oil or wettable powder formulation.

The desired range of concentrations for the test is obtained by further dilution of the master solution or wash.

The ticks are removed from the wash after 10 minutes, dried, and stuck dorsal side down on double-sided adhesive tape.

They remain in this position for 14 days when the proportions of viable eggs laid are determined. From this data a regression line is plotted (concentration against % inhibition of viable egg production) and the IR50 and IR99 (concentrations at which 50% and 99% inhibition respectively of viable egg production occurs).

TABLE I

| Compound | IR50 | IR99 |
|---|---|---|
| Urethane product of Example I | 0.018 | 0.10 |

In a similar manner the IR50 of other compounds of the invention against *Boophilus microplus* Biarra was determined. The results are shown in Table 1a.

TABLE 1a.

| Compound Example No. | IR50 (%) |
|---|---|
| 2 | 0.00061 |
| 3 | 0.004 |
| 4 | (42% inhibition at 0.01%) |

TABLE 1a.-continued

| Compound Example No. | IR50 (%) |
|---|---|
| 5 | (85% inhibition at 0.03%) |
| 6 | 0.03 |
| 7 | (100% inhibition at 0.03%) |

In a further test using the compound of Example 1, the IR50 and IR99 were determined as 0.0054% and 0.029%, respectively.

EXAMPLE 12

Test compounds were formulated in polyethyleneglycol and 0.622 μl was injected into ticks at a site just ventral to the mouth parts. After 14 days the percentage inhibition of viable egg production (IR) was determined. The results are shown in Table 2 below.

TABLE 2

| Compound | % IR |
|---|---|
| Urethane Product of Example I | 80% at 10 mg/ml. |
| | 50% at 1.0 mg/ml. |
| | 100% at 0.1 mg/ml. |

In a similar manner, other compounds of the invention were tested against ticks. The results are shown in Table 2a.

TABLE 2a

| Compound of Example No. | % IR at 1 mg-ml |
|---|---|
| 2 | 80 |
| 3 | 30 |
| 4 | 30 |

EXAMPLE 13—WETTABLE POWDER

| | |
|---|---|
| Active compound | 25.0 parts by weight |
| Kaolin | 69.5 parts by weight |
| Sodium Alkyl Naphthalenesulphonate | 2.5 parts by weight |
| Sodium Salt of condensed Naphthalene Sulphonic acid | 3.0 parts by weight |
| | 100.0 |

EXAMPLE 14—AQUEOUS SUSPENSION

| | |
|---|---|
| Active compound | 50.0 parts by weight |
| Sodium carboxy methyl Cellulose | 0.5 parts by weight |
| Calcium lignosulphonate | 5.0 parts by weight |
| para-Chloro-meta-cresol | 0.2 parts by weight |
| Water | 44.3 parts by weight |
| | 100.0 |

EXAMPLE 15—AQUEOUS SOLUTION.

| | |
|---|---|
| Active compound | 10.0 parts by weight |
| Ethylan KEO | 0.5 parts by weight |
| Deionised water | 89.5 parts by weight |
| | 100.0 |

EXAMPLE 16—WATER-MISCIBLE OIL

| | |
|---|---|
| Active compound | 10.0 parts by weight |
| Ethylan KEO | 20.0 parts by weight |

EXAMPLE 17—PASTE

| | |
|---|---|
| Active compound | 45.0 parts by weight |
| Glycerol | 5.0 parts by weight |
| Xanthan Gum | 2.5 parts by weight |
| Methyl para-Hydroxy-Benzoic Acid | 0.2 parts by weight |
| Fine Silica | 5.0 parts by weight |
| Water | 42.3 parts by weight |
| | 100.0 |

EXAMPLE 18—POUR-ON

| | |
|---|---|
| Active compound | 2.0 parts by weight |
| Corn oil | 83.0 parts by weight |
| Iso-propanol | 15.0 parts by weight |
| | 100.0 |

EXAMPLE 19—DUST

| | |
|---|---|
| Active compound | 1.0 parts by weight |
| Talc | 99.0 parts by weight |
| | 100.0 |

EXAMPLE 20—GREASE

| | |
|---|---|
| Active compound | 1.5 parts by weight |
| White petroleum jelly | 8.5 parts by weight |
| | 100.0 |

"Esso 200"  70.0 parts by weight
         100.0

We claim:

1. A compound of formula (I):

$$R^3\text{-Ar-}X-CH(R)-\underset{\underset{S}{\parallel}}{C}-NH-CH_2-CH_2-N(R^4)(R^5) \quad (I)$$

wherein $R^1$, $R^2$ and $R^3$ are the same or different and are selected from hydrogen, alkyl of 1 to 20 carbon atoms, alkoxy of 1 to 20 carbon atoms, halo, cyano and trifluoromethyl, or two of $R^1$, $R^2$ and $R^3$ are linked to form a 3 or 4 carbon atom group;

X is O or NA where A is hydrogen or alkyl of 1 to 20 carbon atoms:

R is hydrogen or alkyl of 1 to 20 carbon atoms;

$R^4$ is hydrogen; unsubstituted or substituted alkyl of 1 to 20 carbon atoms where the substituents are selected from halo, hydroxy, cyano, alkoxy, phenoxy, naphthyloxy, alkylthio, phenylthio and naphthylthio; alkynyl, alkenyl or haloalkenyl of 3 to 20 carbon atoms saturated in the 1-position; or unsubstituted or substituted phenyl, phenylalkyl, naphthyl or naphthylalkyl where the substituents are selected from alkyl, alkoxy, halo, cyano and trifluoromethyl; and $R^5$ is a group $$-C\underset{\underset{R^6}{\diagdown}}{\overset{\overset{B}{\diagup\!\!\!\!\!\diagup}}{\phantom{C}}}$$

where B is O, S or $NR^7$ where $R^7$ is hydrogen, cyano, alkoxy, alkyl or substituted or unsubstituted phenyl, naphthyl, phenylalkyl or naphthylalkyl where the substituents are selected from alkyl, alkoxy, halo, cyano and trifluoromethyl; and $R^6$ is hydrogen or a group $R^8$, $OR^8$, $SR^8$ or $NR^9R^{10}$ where $R^8$ is alkyl, alkenyl, or substituted or unsubstituted phenyl, naphthyl, phenylalkyl, naphthylalkyl, phenoxyalkyl or naphthyloxyalkyl where the substituents are selected from alkyl, alkoxy, halo, cyano and trifluoromethyl; and $R^9$ and $R^{10}$ are the same or different and are selected from hydrogen, alkyl and substituted or unsubstituted phenyl, naphthyl, phenylalkyl or naphthylalkyl where the substituents are selected from alkyl, alkoxy, halo, cyano and trifluoromethyl; or an acid addition salt thereof when X is NA or B is $NR^7$.

2. A compound according to claim 1 which is of formula (II):

$$R^3\text{-Ar-}X-CH(R)-\underset{\underset{S}{\parallel}}{C}-NH-CH_2-CH_2-NH-COOY \quad (II)$$

wherein $R^1$, $R^2$, $R^3$, X and R are as defined in claim 1 and Y is alkyl of 1 to 20 carbon atoms, alkenyl of 2 to 20 carbon atoms, phenyl, naphthyl, phenylalkyl or naphthylalkyl.

3. A compound according to claim 1 wherein X is O or NH.

4. A compound according to claim 2 wherein X is O or NH.

5. A compound according to claim 1 wherein R is hydrogen or methyl.

6. A compound according to claim 2 wherein R is hydrogen or methyl.

7. A compound according to claim 3 wherein R is hydrogen or methyl.

8. A compound according to claim 1 wherein $R^1$ and $R^2$ are in the 2- and 3- positions, respectively, and $R^3$ is hydrogen.

9. A compound according to any one of claims 1 to 8 wherein $R^1$ and $R^2$ are the same or different and are selected from halo and alkyl.

10. A compound according to claim 8 wherein $R^1$ and $R^2$ are both methyl.

11. A compound according to any one of claims 1 to 8 or claim 10 wherein $R^4$ is hydrogen.

12. A compound according to any one of claims 1, 3, 5, 7, 8 or 10 wherein B is S and $R^6$ is unsubstituted or substituted phenylamino wherein the substituents are selected from alkyl, alkoxy, halo, cyano and trifluoromethyl.

13. A compound according to any one of claims 1, 3, 5, 7, 8 or 10 wherein B is O and $R^6$ is methyl.

14. N-[(2,3-Dimethylphenoxy)-thioacetyl]-N'-ethoxycarbonylethane-1,2-diamine.

15. A compound selected from
N-[(2,3-dimethylphenoxy)thioacetyl]-N'-phenylthiocarbamoyl-1,2-diaminoethane;
N-[(2,3-dimethylphenoxy)-thioacetyl]-N'-(benzyloxycarbonyl)-ethane-1,2-diamine;
N-[(2,3-dimethylphenoxy)-thioacetyl]-N'-(4-chlorophenylcarbamoyl)-ethane-1,2-diamine;
N-[(2,3-dimethylphenoxy)-thioacetyl]-N'-(methylthiocarbamoyl)-ethane-1,2-diamine;
N,N'-bis[(2,3-dimethylphenoxy)-thioacetyl]-ethane-1,2-diamine; and
N-[(2,3-dimethylphenoxy)thioacetyl]-N'-acetyl-ethane-1,2-diamine.

16. An arthropodicidal formulation comprising an arthropodicidally effective amount of a compound of formula (I):

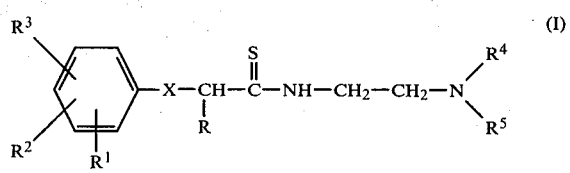

wherein
$R^1$, $R^2$ and $R^3$ are the same or different and are selected from hydrogen, alkyl, alkoxy, halo, cyano and trifluoromethyl or two of $R^1$, $R^2$ and $R^3$ are linked to form a 3 or 4 carbon atom group;
X is O or NA where A is hydrogen or alkyl;
R is hydrogen or alkyl;
$R^4$ is hydrogen; alkyl; substituted alkyl where the substituents are selected from halo, hydroxy, cyano, alkoxy, aryloxy, alkylthio and arylthio; alkynyl; alkenyl; haloalkenyl; aralkyl; aryl; or substituted aralkyl or aryl where the substituents are selected from alkyl, alkoxy, halo, cyano and trifluoromethyl; and
$R^5$ is a group

where B is O, S or $NR^7$ where $R^7$ is hydrogen, cyano, alkoxy, alkyl, aryl, aralkyl or substituted aryl or aralkyl where the substituents are selected from alkyl, alkoxy, halo, cyano and trifluoromethyl; and $R^6$ is hydrogen or a group $R^8$, $OR^8$, $SR^8$ or $NR^9R^{10}$ where $R^8$ is alkyl, aryloxyalkyl, alkenyl, aralkyl, aryl or substituted aryl, aryloxyalkyl or aralkyl where the substituents are selected from alkyl, alkoxy, halo, cyano and trifluoromethyl; and $R^9$ and $R^{10}$ are the same or different and are selected from hydrogen, alkyl, aralkyl, aryl and substituted aryl or aralkyl where the substituents are selected from alkyl, alkoxy, halo, cyano or trifluoromethyl; or an acid addition salt thereof when X is NA or B is $NR^7$ and a carrier therefor.

17. A formulation according to claim 16 wherein the compound of formula (I) is of formula (II):

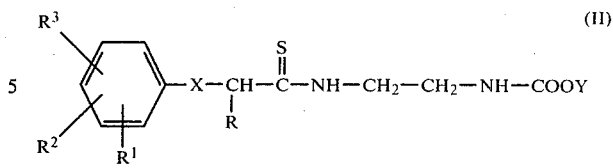

wherein $R^1$, $R^2$, $R^3$, X and R are as defined in claim 18 and Y is alkyl, alkenyl, aryl or aralkyl; or an acid addition salt thereof when X is NA.

18. A formulation according to claim 16 wherein X is O or NH.

19. A formulation according to claim 17 wherein X is O or NH.

20. A formulation according to claim 18 wherein R is hydrogen or methyl.

21. A formulation according to claim 19 wherein R is hydrogen or methyl.

22. A formulation according to claim 16 wherein $R^1$ and $R^2$ are in the 2- and 3- positions, respectively, and are each halo or alkyl and $R^3$ is hydrogen.

23. A formulation according to claim 17 wherein $R^1$ and $R^2$ are in the 2- and 3- positions, respectively, and are each halo or alkyl and $R^3$ is hydrogen.

24. A formulation according to claim 16 wherein $R^4$ is hydrogen.

25. A formulation according to claim 17 wherein $R^4$ is hydrogen.

26. A formulation according to claim 16 wherein the compound of formula (I) is selected from:
N-[(2,3-dimethylphenoxy)thioacetyl]-N'-ethoxycarbonylethane-1,2-diamine;
N-[(2,3-dimethylphenoxy)thioacetyl]-N'-phenylthiocarbamoyl-1,2-diaminoethane;
N-[(2,3-dimethylphenoxy)-thioacetyl]-N'-(benzyloxycarbonyl)-ethane-1,2-diamine;
N-[(2,3-dimethylphenoxy)-thioacetyl]-N'-(4-chlorophenylcarbamoyl)-ethane-1,2-diamine;
N-[(2,3-dimethylphenoxy)-thioacetyl]-N'-(methylthiocarbamoyl)-ethane-1,2-diamine;
N,N'-bis[(2,3-dimethylphenoxy)-thioacetyl]-ethane-1,2-diamine; and
N-[(2,3-dimethylphenoxy)thioacetyl]-N'-acetyl-ethane-1,2-diamine.

27. A formulation according to any one of claims 16 to 26 comprising from 1 to 80% of a compound of formula (I), said formulation being in the form of an aqueous or non-aqueous solution or suspension, water-miscible oil, wettable powder, dust, powder, granules, aerosol, foam, impregnated article, paste, grease or gel.

28. A method for controlling arthropod pests comprising the application to the pests or their environment of an effective amount of a compound of formula (I):

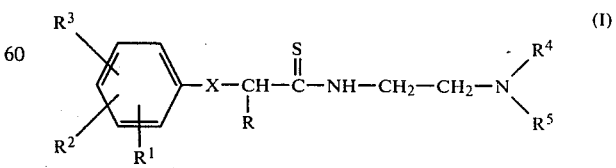

wherein
$R^1$, $R^2$ and $R^3$ are the same or different and are selected from hydrogen, alkyl, alkoxy, halo, cyano and trifluoromethyl or two of $R^1$, $R^2$ and $R^3$ are linked to form a 3 or 4 carbon atom group;

X is O or NA where A is hydrogen or alkyl;

R is hydrogen or alkyl;

$R^4$ is hydrogen; alkyl; substituted alkyl where the substituents are selected from halo, hydroxy, cyano, alkoxy, aryloxy, alkylthio and arylthio; alkynyl; alkenyl; haloalkenyl; aralkyl; aryl; or substituted aralkyl or aryl where the substituents are selected from alkyl, alkoxy, halo, cyano and trifluoromethyl; and $R^5$ is a group

where B is O, S or $NR^7$ where $R^7$ is hydrogen, cyano, alkoxy, alkyl, aryl, aralkyl or substituted aryl or aralkyl where the substituents are selected from alkyl, alkoxy, halo, cyano and trifluoromethyl; and $R^6$ is hydrogen or a group $R^8$, $OR^8$, $SR^8$ or $NR^9R^{10}$ where $R^8$ is alkyl, aryloxyalkyl, alkenyl, aralkyl, aryl or substituted aryl, aryloxyalkyl or aralkyl where the substituents are selected from alkyl, alkoxy, halo, cyano and trifluoromethyl; and $R^9$ and $R^{10}$ are the same or different and are selected from hydrogen, alkyl, aralkyl, aryl and substituted aryl or aralkyl where the substituents are selected from alkyl, alkoxy, halo, cyano or trifluoromethyl; or an acid addition salt thereof when X is NA or B is $NR^7$ or a formulation comprising said aforementioned compound or salt and a carrier therefor.

29. A method according to claim 28 wherein the compound of formula (I) is of formula (II):

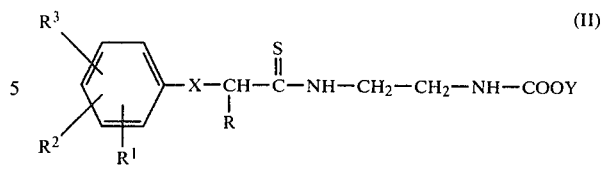

wherein $R^1$, $R^2$, $R^3$, X and R are as defined in claim 30 and Y is alkyl, alkenyl, aryl or aralkyl; or an acid addition salt thereof when X is NA.

30. A method according to claim 28 wherein the compound of formula (I) is selected from:
N-[(2,3-dimethylphenoxy)thioacetyl]-N'-ethoxycarbonylethane-1,2-diamine;
N-[(2,3-dimethylphenoxy)thioacetyl]-N'-phenylthiocarbamoyl-1,2-diaminoethane;
N-[(2,3-dimethylphenoxy)-thioacetyl]-N'-(benzyloxycarbonyl)-ethane-1,2-diamine;
N-[(2,3-dimethylphenoxy)-thioacetyl]-N'-(4-chlorophenylcarbamoyl)-ethane-1,2-diamine;
N-[(2,3-dimethylphenoxy)-thioacetyl]-N'-(methylthiocarbamoyl)-ethane-1,2-diamine;
N,N'-bis[(2,3-dimethylphenoxy)-thioacetyl]-ethane-1,2-diamine; and
N-[(2,3-dimethylphenoxy)thioacetyl]-N'-acetylethane-1,2-diamine.

31. A method according to claim 28 wherein the compound is applied at a concentration of from 0.001 to 20%.

32. A method according to any of claims 28 to 31 wherein the pests are of the Order Acarina.

33. An arthropodicidal formulation comprising an effective arthropodicidal amount of the compound of claim 14 and a carrier therefore.

34. A method for controlling arthropod pests comprising the application to the pests or their environment an effective arthropodicial amount of the compound of claim 14.

35. The method of claim 34 in which the compound is applied in a suitable carrier therefore.

36. The compound of claim 2 wherein $R^1$, and $R^2$ are the same or different and are selected from halo and alkyl.

37. The compound of claim 2 wherein $R^1$ and $R^2$ are in the 2- and 3- positions respectively, and $R^3$ is hydrogen.

38. The compound of claim 2 in which $R^1$ and $R^2$ are both methyl.

39. The compound of claims 2, 4, 6, 36, 37 or 38 wherein Y is alkyl or phenylalkyl.

40. The compound of claims 2, 4, 6, 36, 37 or 38 wherein Y is ethyl.

* * * * *